United States Patent [19]

Lefevre et al.

[11] Patent Number: 5,196,346

[45] Date of Patent: Mar. 23, 1993

[54] REAGENT AND METHOD OF USING SAME FOR AUTOMATICALLY COUNTING BASOPHILIC LEUKOCYTES IN THE BLOOD IN RESISTIVITY VARIATION MEASURING APPARATUS

[75] Inventors: Didier Lefevre, Mantes La Ville; Henri Champseix, Montferrier-Sur-Lez, both of France

[73] Assignee: ABX, Cedex, France

[21] Appl. No.: 651,564

[22] Filed: Feb. 6, 1991

[30] Foreign Application Priority Data

Feb. 13, 1990 [FR] France ................. 90 01660

[51] Int. Cl.$^5$ ............................................. G01N 33/48
[52] U.S. Cl. ........................................................ 436/63
[58] Field of Search .......................................... 436/63

[56] References Cited

FOREIGN PATENT DOCUMENTS 0177137 7/1985 European Pat. Off. .
0316453 5/1988 European Pat. Off. .
8400379 3/1984 PCT Int'l Appl. .

*Primary Examiner*—John W. Rollins
*Attorney, Agent, or Firm*—Birch, Stewart, Kolasch & Birch

[57] ABSTRACT

The invention relates to a reagent and a method of using the same for automatically determining the population of the basophilic leukocytes in the blood. The invention relates more particularly to a new formulation for a differential lysing reagent that lyses all the blood cells except for the basophils, particularly suitable for the measuring principle based on resistivity measurement, that is to say the concentrations of the constitutents and the pH of the solution are suitable for ensuring good electrical conductivity of the medium. The reagent according to the invention will find an application in apparatus for automatically determining blood formulae by means of resistivity variation measurements.

8 Claims, 1 Drawing Sheet

REAGENT AND METHOD OF USING SAME FOR AUTOMATICALLY COUNTING BASOPHILIC LEUKOCYTES IN THE BLOOD IN RESISTIVITY VARIATION MEASURING APPARATUS

The invention relates to the analysis of blood formula by counting and discriminating at least one leukocyte sub-population. The invention relates more particularly to a reagent and a method of using the same for counting basophilic granulocytes in flow cytometry using resistivity measurement.

The diagnostic importance of precisely determining the different leukocyte populations has long been recognized; indeed, the occurrence of abnormal leukocyte ratios can be correlated with the occurrence of various diseases.

The traditional methods of specific staining and observation through the microscope has already made it possible to distinguish between all the types of leukocytes, that is to say the granulocytes (basophils, eosinophils and neutrophils) and the agranulocytes (monocytes and lymphocytes), but it takes a very long tome to implement these methods.

There are already various apparatus on the market that can be used for counting the different total blood leukocyte populations, and a number of reagents and staining agents have been developed for use in such apparatus.

It is thus possible to measure the size of the cells, after differential lysis of their cytoplasms, either by measuring variations in resistivity (as described, for example, in patent WO 84/03771) or by measuring optical diffraction (as described, for example, in U.S. Pat. No. 3,740,143); it is also possible to carry out specific staining (enzymatic or otherwise) of the different cell types and, in particular, of the three types of granulocyte, and then measure the sizes and optical densities of cells at different wavelengths (U.S. Pat. No. 3,740,143).

Counting the basophilic granulocytes is a particularly delicate operation as this type of cell represents only 0.5 to 1% of the white blood corpuscles.

The basophilic granulocytes are distinguished by their high heparin content, heparin being a sulphated polysaccharide that can be revealed by staining agents of the phthalocyanide family, such Alcian blue or Astra blue.

The staining of the basophilic granulocytes with neutral red, traditionally used in the manual method, can also be combined with the differential lysis treatment of the leukocytes for use in an automatic apparatus (U.S. Pat. No. 3.740,143).

European patent application 0 177 137 describes a lytic reagent that permits the progressive destruction of all the blood cells with the exception of the basophils. This reagent damages the cell membranes, which leads to the escape of the cytoplasm. At different time intervals, the different cell types are observed to disappear, i.e., in succession, the erythrocytes, lymphocytes, eosinophils, neutrophils and the monocytes. After 80 seconds, only the basophils have retained their normal size and morphology. The active principle of this reagent is a mixture of surfactant and diluted acid. This mixture must be used within a narrow pH range of between 1.8 and 2.3.

This reagent yields good results in an optical reading type counting apparatus, but it is not suited to measurements based on resistivity; in particular, it poses a major problem with regard to the clogging of the counting orifice of the apparatus before destruction of the membranes of the red blood corpuscles is complete.

The principle of cell counting using resistivity is based on providing an electric field in which a constant current is maintained; the passage of a cell through this field causes an increase in the voltage needed to maintain the current constant (according to Ohm's law). The voltage pulse generated by the passage of a cell (and which constitutes the measurement recorded by the apparatus) is proportional to the resistance presented, hence to the volume of the cell, regardless of its shape. This method of detection does not, therefore, apply only to cells that have undergone prior treatment (more particularly by differential cytolysis) in order to obtain very clear discrimination of the sizes of the sub-populations.

This method is very simple to use as it is not necessary to stain the cells.

DESCRIPTION OF DRAWINGS

A histogram representative of a normal blood sample presented in FIG. 1A: curve 1.1 represents the determination carried out in medium containing neither SDS nor Astra blue and with a pH of 1.9; the red blood corpuscle membranes are observed to impede resistivity measurement.

Figure 1A:
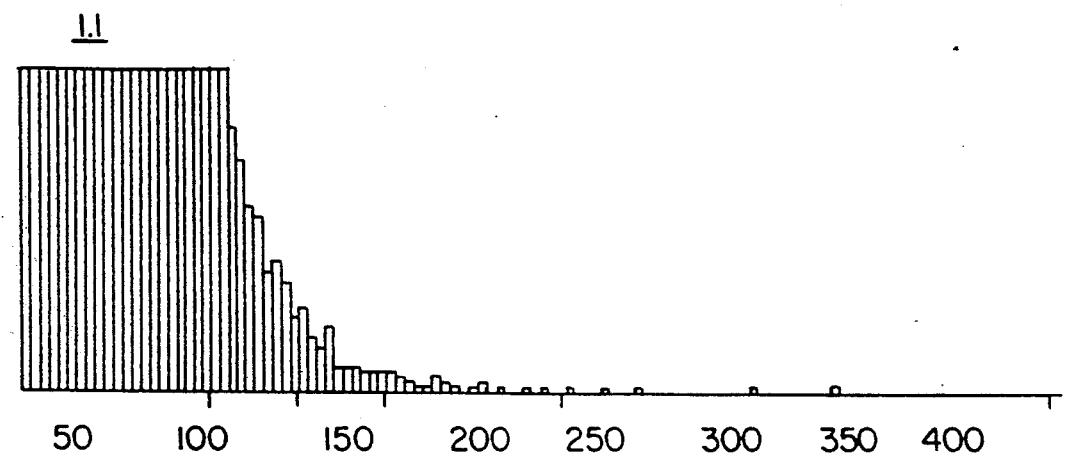
FIG. 1B: curve 1.2 represents the determination carried out in the reagent according to the present invention; area A corresponds to the nuclei of the lysed cells, while are B corresponds to the basophilic leukocytes the cytoplasm of which is intact.
Figure 1B:
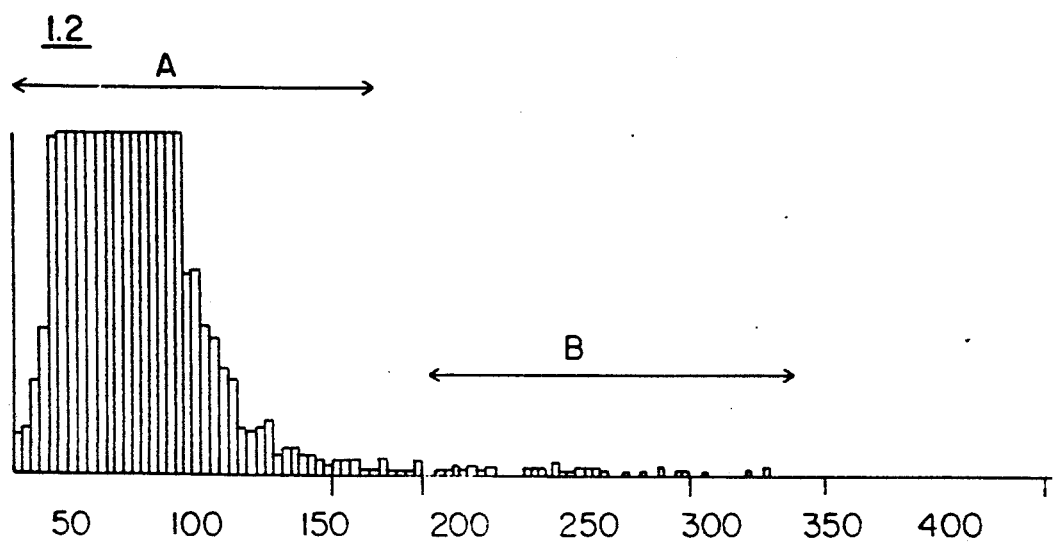

The Applicant has developed a new formulation for the differential lysing reagent which preserves the basophilic granulocytes so as to permit its use in a resistivity measurement apparatus.

Thus, the reagent according to the present invention includes a polyoxyethylene ether type surfactant (such as Brij 35 or 23-lauryl-ether) at a concentration of between 1 and 5 g/l and a mixture of phthalic acid at a concentration of 0.5 to 1.5 g/l and 0.25 mM HCl. The relative concentration of the different constituents are adjusted to obtain a pH of between 2.5 and 3.2.

The Applicant has found that detection sensitivity was improved by adding SDS (sodium dodecyl sulphate) to the reagent, at a concentration of between 50 and 300 mg/l, as a protein denaturing agent, which reduces the formation of deposits in the measuring instrument; moreover, the SDS accelerates the lysis of the cells.

An anti-oxidizing agent such as butylated hydroxytoluene or BHT ($C_{11}H_6O$-di-tert-butyl-4-methylphenol) at a concentration of 10 to 30 mg/l can also be advantageously added to the reagent.

Thus, according to a preferred form of embodiment of the invention, the reagent includes the following constituents:

1 to 5 g/l of Brij 35
0.5 to 1.5 g/l of phthalic acid
0.25 mM HCl
50 to 300 mg/l of SDS
10 to 30 mg/l of butylated hydroxytoluene According to a form of embodiment of the invention, Astra blue can also be added to the reagent, this being a specific staining agent for heparin granules that improves their fixing.

The invention also relates to a method for using this reagent in an automatic flow cytometry apparatus, using resistivity measurement, for determination of the basophilic leukocytes.

The method according to the invention includes contacting the blood sample to be studied and the reagent in a thermostatically controlled chamber at a temperature of between 30° and 40° C. for a duration of 5 to 30 seconds (the temperature and the contact time being adjusted, in inverse relationship to one another).

The method then includes detection of the cells that are intact, that is to say the basophils, by means of resistivity measurement in a suitable detection apparatus, and recording these measurements in the form of a histogram.

The figure is a representative histogram obtained by applying the method according to the invention to a sample of normal blood.

The following example illustrates a form of embodiment of the invention without, however, limiting the scope thereof.

EXAMPLE

The following concentration of the different constituents have been calculated for the preparation of one liter of reagent:

| Brij 35 | 2.5 g |
| phthalic acid | 0.9 g |
| HCl—1N | 0.25 ml |
| SDS | 200 mg |
| butylated hydroxytoluene | 25 mg |
| Distilled water adjusted to | 1 liter |

The pH is maintained at 2.7 (between 2.5 and 3.2).

Astra blue can be added to the reagent at a concentration of 10 to 100 mg/l; under the pH conditions chosen, Astra blue is soluble and stable.

This reagent can be used in any apparatus for automatically counting the blood corpuscles based on the principle of resistivity measurement (for example ABX model 504F). The electrode voltage is set to 100 V.

The apparatus is adjusted to contact a 15 µl total blood sample with 2 ml of reagent. This mixture is produced in a thermostatically controlled chamber at a temperature of 40° C. with a contact time of 17 seconds. (The same result can be obtained by reducing the temperature and increasing the contact time, and vice versa).

The reagent causes immediate lysis of the red blood cells, and then the gradual lysis of all the other types of cell, with the exception of the basophilic granulocytes. After 30 seconds' contact at 40° C., it can be verified that the morphology of the basophils remains intact by manual determination and observation through the microscope. When the reagent contains Astra blue, the staining of the basophils is proportional to the concentration of Astra blue used.

We claim:

1. A differential lysing reagent for counting basophilic leukocytes in the blood in an automatic analyzer using resistivity measurement, which comprises:
    a polyoxyethylene ether type surfactant,
    a phthalic acid-HCl mixture,
    SDS (sodium dodecyl sulphate)
    a butylated hydroxytoluene type anti-oxidizing agent,
        in that its pH is between 2.5 and 3.2 and that it is electrically conductive.

2. The reagent according to claim 1, wherein said surfactant is Brij 35 at a final concentration of between 1 and 5 g/l.

3. The reagent according to claim 1 wherein said acid mixture includes phthalic acid at a final concentration of 0.5 to 1.5 g/l and HCl at a final concentration of 0.25 mM.

4. The reagent according to claim 1, wherein said SDS is present at a final concentration of between 50 and 300 mg/l.

5. The reagent according to claim 1, wherein said butylated hydroxytoluene is present at a final concentration of 10 to 30 mg/l.

6. The reagent according to claim 1, further comprising Astra blue at a concentration of between 10 and 100 mg/l.

7. A method of counting the population of basophilic leukocytes contained in the blood in an automatic flow cytometry apparatus, which comprises:
    contacting a blood sample with a reagent according to any one of claims 1 to 6, in a thermostatically controlled chamber,
    detecting said basophilic leukocytes, by measuring variations in resistivity, and
    recording these measurements in the form of a histogram.

8. The method according to claim 7, wherein said blood is contacted with said reagent at a temperature of between 30° and 40° C. and for a period of 5 to 30 seconds.

* * * * *